United States Patent [19]

Magnusen et al.

[11] Patent Number: 5,129,406
[45] Date of Patent: Jul. 14, 1992

[54] METHOD FOR USING AN INFANT GARMENT WITH CROSSED OVER ARM POSITIONING SLEEVES

[76] Inventors: Debbe A. Magnusen; David A. Magnusen, both of 1075 Corona La., Costa Mesa, Calif. 92626

[21] Appl. No.: 692,163

[22] Filed: Apr. 26, 1991

[51] Int. Cl.⁵ .................................. A61F 5/37
[52] U.S. Cl. ........................ 128/873; 128/872; 128/869; 128/845; 2/69.5
[58] Field of Search .................. 128/869–875, 128/845, 846, DIG. 15; 2/DIG. 7, 69.5, 83, DIG. 6, 80, 111, 81, 75

[56] References Cited

U.S. PATENT DOCUMENTS

| | | | |
|---|---|---|---|
| 881,640 | 3/1908 | Wimmel . | |
| 965,640 | 1/1910 | Mercey . | |
| 1,373,378 | 3/1921 | Backman . | |
| 1,944,451 | 1/1934 | Newman | 128/134 |
| 2,030,091 | 2/1936 | Behringer | 128/873 |
| 2,431,603 | 11/1947 | Zito | 2/114 |
| 2,465,622 | 3/1949 | Widetsky | 128/873 |
| 2,538,420 | 1/1951 | Junghans | 2/69 |
| 2,675,557 | 4/1954 | Kempner, Jr. | 2/114 |
| 3,034,132 | 5/1962 | Landsberger et al. | 2/69.5 |
| 3,181,530 | 5/1965 | Storey | 128/134 |
| 3,739,399 | 6/1973 | Sheahon | 2/69.5 |
| 3,901,229 | 8/1975 | Hensel et al. | 128/134 |
| 4,206,512 | 6/1980 | Osborne | 2/69.5 |
| 4,451,932 | 6/1984 | Wagemann et al. | 2/80 |
| 4,502,153 | 3/1985 | Lapedes | 2/81 |
| 4,611,353 | 9/1986 | Als et al. | 2/69 |
| 4,759,082 | 7/1988 | Mulligan | 2/75 |
| 4,897,885 | 2/1990 | Lunt | 2/69.5 |
| 4,901,371 | 2/1990 | Christians | 2/83 |
| 4,971,073 | 11/1990 | Schneider | 128/874 |
| 4,998,296 | 3/1991 | Stames | 2/69.5 |
| 5,016,650 | 5/1991 | Marlar | 128/869 |

FOREIGN PATENT DOCUMENTS

7600862  8/1976  Netherlands .

OTHER PUBLICATIONS

Tim Healey, "Pre-Term Infant Care", circa 1985.

*Primary Examiner*—Robert A. Hafer
*Assistant Examiner*—David J. Kenealy
*Attorney, Agent, or Firm*—Knobbe, Martens, Olson & Bear

[57] ABSTRACT

An infant garment, particularly for premature and drug addicted infants, that is comprised of a saclike body with two extended sleeves that cross over each other, wrap around the child, and then attach in the back. The garment places the child's arms in the midline position and constrains them to prevent unnecessary motor releases. The garment is designed to allow for passage of test leads and tubes through the opening in the front of the garment while the garment remains closed. The garment swaddles the infant in warm clothing and will enable the child to rest more easily.

7 Claims, 3 Drawing Sheets

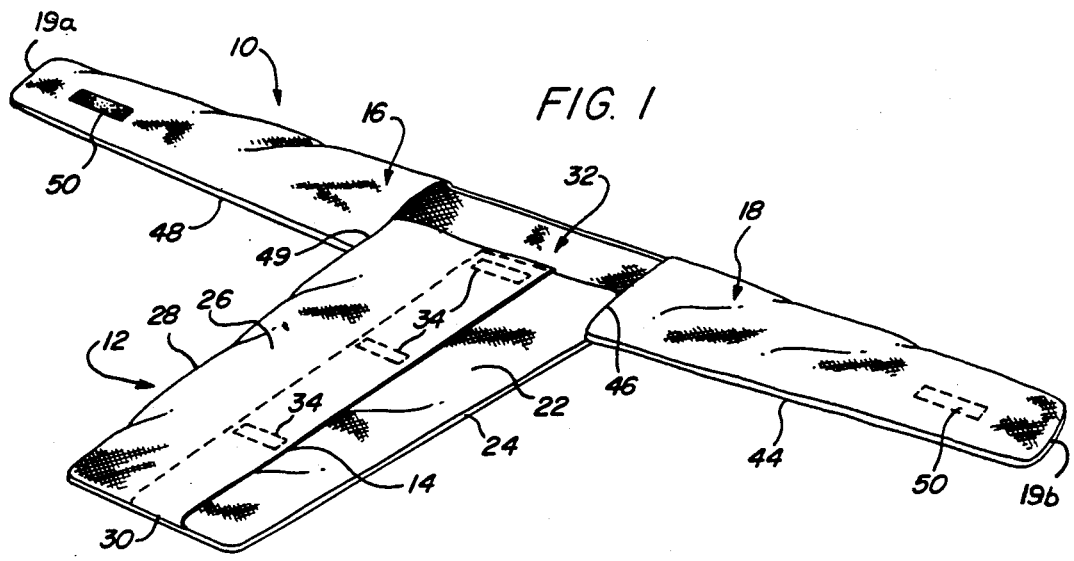
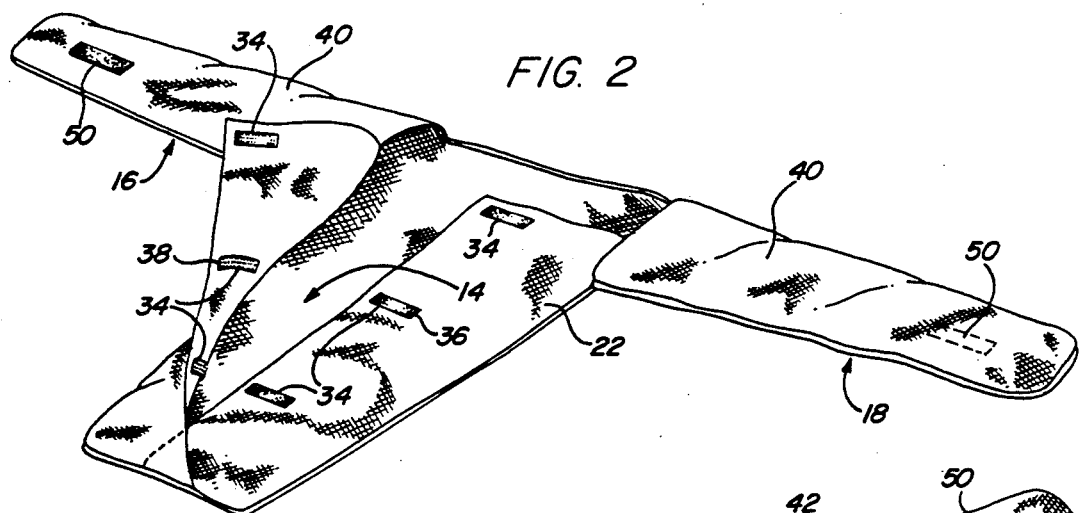
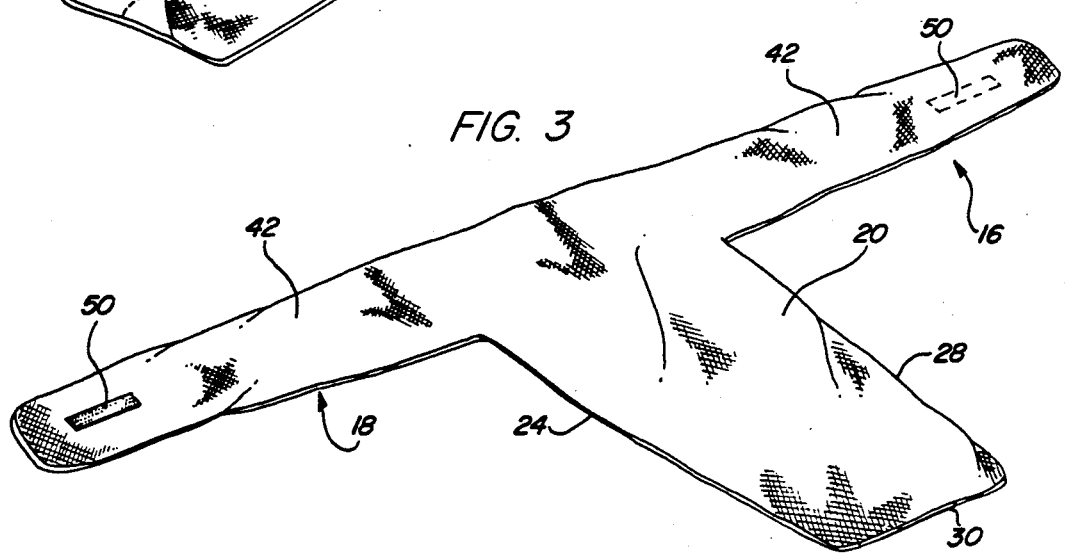

METHOD FOR USING AN INFANT GARMENT WITH CROSSED OVER ARM POSITIONING SLEEVES

FIELD OF THE INVENTION

The present invention is related to infant clothing and more particularly to a garment used for infants to provide both warmth and restraint in order to enable the infant to rest.

BACKGROUND OF THE INVENTION

In our society there is an increasing number of babies that are born to drug addicted mothers. These infants suffer from a number of special problems that normal babies do not encounter, because they are born with the same drug addictions that their mothers suffered from. Infants born with drug addictions have a tendency to tremor due to drug withdrawals. These tremors over-stimulate the infant and make rest nearly impossible. Treatment of drug addicted babies include three different methods of calming the newborn infant. These methods are swaddling the infant, holding the infant with restraint of the arms to prevent unnecessary motor releases, and positioning the infant in the midline position.

In addition, babies suffering from drug addiction are often born prematurely and are of low birth weight. The overactive trembling associated with drug withdrawals not only prevents the infant from resting, but it burns off additional calories and makes all important weight gain difficult. Most premature babies especially those born with drug addictions, require extensive medical care. Commonly, these babies are connected to multiple electrical heart leads, G.T. tubes, etc.

It is also very important that newborn babies be kept warm, as their bodies are very susceptible to variations in temperature. Exposure to cold air can lead to colds which are quite serious to newborn babies. Additionally, exposure can cause hypothermia in newborns as their thermoregulatory mechanisms are unstable. Both of these situations are even more serious in premature babies and babies born to drug addicted parents, as their immune systems are not fully developed yet.

SUMMARY OF THE INVENTION

The present invention provides a novel garment for drug addicted and premature babies which keeps the child warm, calms the child by placing it in the midline position, and allows access of monitoring leads and tubes to the infant. The preferred embodiment of this invention includes a saclike garment having an open pouch in which the infant is laid. Two sleeves extend past the length of the infant's arms and wrap around the back of the infant where the sleeves can be quickly and easily attached together using a VELCRO ® fastener.

These sleeves position the infant's arms in front of the infant in a crossed over position with the elbows bent. This crossed over positioning of the arms in front of the infant, with the baby free to curl up its body, is often referred to as the midline position and it is the position that the infant is in when it is still in the mother's womb. The midline position results in the infant's central nervous system reaching its calmest state and helps the baby sleep longer and deeper. Calming the infant is especially important in the care of drug addicted babies, because they are constantly over stimulated. Additionally, this is the time when the infant's nervous system matures and organizes, so it is important to ensure the infant has sufficient rest periods free from over stimulation. Providing a means for calming the baby after stimulus, helps keep the heart rate and blood-pressure down which should prevent unnecessary strokes and seizures.

A significant feature of the garment's construction in accordance with the invention is that the sleeves of the garment not only position the infant's arms, but help to restrain the arms. Drug addicted children are prone to tremors due to withdrawals which burn off a significant amount of calories. By providing restraint of the arms, the garment helps to control the tremors and allows for proper weight gain. If the infant is so small that crossing the sleeves and attaching the VELCRO ® fasteners in back does not properly restrain the arms, the arms may be crossed over each other and the sleeves may be tied in a knot in the front and then attached in the back using the fastener. This tying of the sleeves takes up the extra slack in the sleeves and properly restrains the infant's arms.

The open pouch of the garment is specifically designed to allow for limited movement of the feet, so the infant can obtain the midline position, but the legs are restrained within the main body to prevent too much unnecessary movement. Normally a trembling infant will thrash around so much that it will uncover itself, if a normal blanket was used, but the enclosed saclike body of the present invention keeps the baby fully covered. Keeping the infant warm is not only important in preventing illness, but it is necessary in aiding the infant's development. One advantage of the garment is that energy that would be expended in order to stabilize the infant's temperature, can be saved and used to foster their growth and development. If additional access to the legs are required to allow for diaper changing, more freedom of movement etc., the infant's legs can be removed from the body of the garment, while its arms remain in a restrained position.

The main body portion of the garment contains a frontal opening all the way down the center of the garment in order to allow easy insertion, removal, and access to the infant. Two VELCRO ® fasteners provide for securing the frontal opening of the garment in a closed position to ensure that the infant is adequately covered and kept warm. The VELCRO ® fasteners were chosen because they provide an easy fastening method, but also provide for an easy removal process in case any emergency medical treatment is necessary. The VELCRO ® fasteners are spaced such that necessary heart leads, G.T. tubes etc. may pass through the frontal opening between the fasteners and still remain easily accessible to the doctors, while the garment remains in a closed position to keep the infant warm. An additional feature of the garment is that as it provides access for medical equipment, such as tubes, test leads etc., it also acts as a restraint that prevents the infant from ripping out these tubes etc. by excessive arm and leg movement.

The present invention has a significant advantage over prior art infant's clothing in that it provides the three suggested methods of calming a newborn by use of a single garment. The garment swaddles the infant by providing a body style that wraps the infant in warm clothing that can not be easily kicked off by the infant. The VELCRO ® fasteners on the sleeves help to constrain the arms to prevent unnecessary motor releases. Finally, the saclike body and sleeve design help to position the infant in the midline position. Providing a means to help calm the infant is especially important for the care of drug addicted babies, since the majority of their treatment is aimed at providing them with the rest that they need.

In addition to infants suffering from drug addiction, the present invention has also been found to materially assist in caring for irritable babies, babies suffering from celiac disease, as well as premature babies.

BRIEF DESCRIPTION OF THE DRAWINGS

FIG. 1 is a perspective view of the front of the infant garment of the present invention.

FIG. 2 is perspective view of the infant garment with the frontal opening shown in the open position.

FIG. 3 is a perspective view of the back surface of the garment illustrated in FIGS. 1-2.

DETAILED DESCRIPTION OF THE INVENTION

Figure 4:
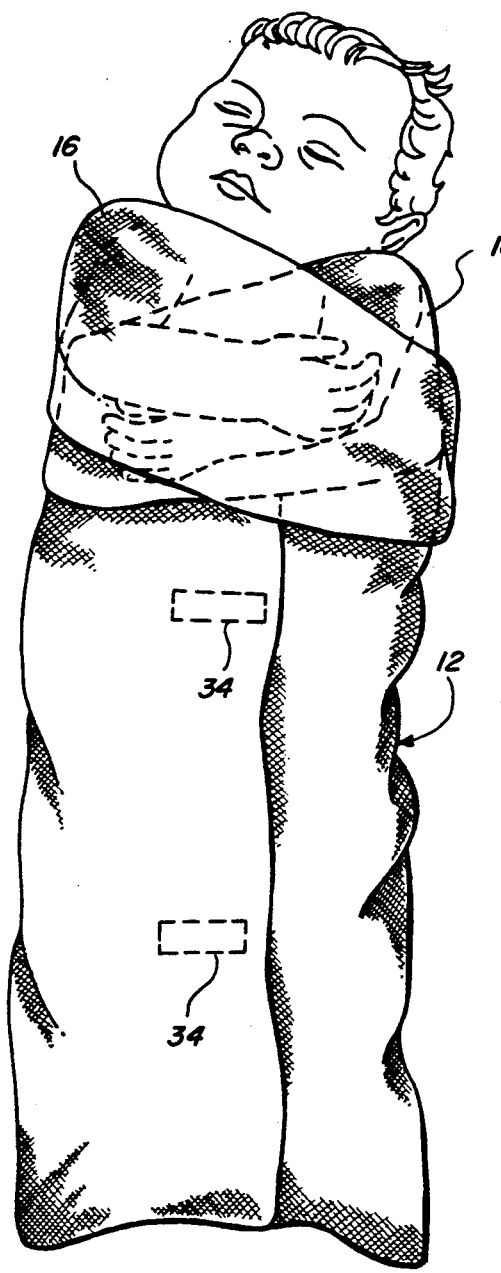
FIG. 4 is a front view of an infant in the garment illustrating the positioning of the infant's arms within the sleeves.

Referring to FIGS. 1-3, the preferred embodiment of the invention is a saclike garment 10 that has a rectangularly shaped main body 12, an opening 14 down the front of the main body 12, two extended sleeves 16, 18 that are too long for the infant's arms and can wrap around the back of the infant where the sleeves 16, 18 can be attached together. The remote ends 19a, 19b of these extended sleeves 16, 18 are closed on the ends, so that when the infant's arms are placed inside, the infant's arms will be restrained within the sleeves 16, 18. The preferred embodiment of the garment 10 is made from a soft polyester flannel material that is flame retardant. This material will keep the child warm and will be gentle up against the infant's skin.

As shown in FIGS. 1-3, the main body 12 of the garment 10 includes a back panel 20 sewn to two opposing, overlapping pieces of material, the front right panel 22 along the seam 24, and the front left panel 26 along the seam 28, and the bottom section of the body 12 is closed along the seam 30. The two front panels 22, 26 are advantageously smaller then the corresponding main rectangular potion of the back panel 20 so when the two panels 22, 26 are attached to the back panel 20, the do not reach the top of the garment and thus form a large open neck area 32. The neck area 32 is designed so that when the infant is placed inside the garment his or her head is in full view. When the two front pieces 22, 26 overlap, they form the opening 14 down the front of the main body 12.

As shown in FIG. 2, the frontal opening 14 is advantageously closed by a plurality of pressure sensitive strip fasteners 34. These strip fasteners are formed from two pieces of nylon material, the first piece made of a plurality of soft eyelets 36, the second piece composed of a plurality of small raised hooks making the surface appear rough 38. When the two pieces are pressed together, the small hooks attach themselves to the small eyelets and connect the two pieces together. These fasteners are commonly sold under the trademark VELCRO ®, and are referred to as such throughout this application. In the preferred embodiment there are three VELCRO ® fasteners generally labeled as 34 which are placed with approximately six inches of space between each fastener, the first fastener 34 being placed six inches from the bottom of the garment 10. The soft eyelet part 36 of each of the VELCRO ® fasteners 34 is placed on the front right panel 22 and the other rough hooked part 38 of the VELCRO ® fastener 34 is placed on the front left panel 26. When the front left panel 26 overlaps the front right panel 22, the two pieces of the VELCRO ® fastener 34 will match up and, when pressed, will fasten together. The spacing of the fasteners is designed to allow for passage of heart leads, tubes etc. through the frontal opening 14 between the fasteners 34. These fasteners 34 provide a means to keep the frontal opening 14 in a secured closed position to keep the infant warm.

The sleeve 18 is formed by sewing a generally rectangular piece of material 40, referred to as the sleeve panel, to the corresponding rectangular section 42 of the back panel 20. The two pieces 40 and 42 are sewn together along the entire outer lengths of the sleeve panel 40 along seam 44, and thus encloses the remote end 19b of the sleeve 18. The sleeve panel 40 is then attached to the front right panel 22 along seam 46. Sleeve 16 is made in a similar manner by sewing the sleeve panel 40 along seam 48 and attaching it to the front left panel 26 along seam 49. Advantageously, the sleeves are only slightly shorter than the length of the back panel 20. The completed sleeves 16, 18 are thus substantially longer than the arms of the infant so that the ends of the sleeve extend past the length of the arms and reach around the back of the infant while the arms remain crossed in front. See FIG. 4 to illustrate the crossed-over position.

The sleeves are attached to each other behind the back of the infant using a VELCRO ® fastener 50 to hold the infant's arms in the crossed-over position. As shown in FIG. 3, the VELCRO ® fastener 50 is sewn such that the rough hooked side is attached to the front of sleeve 16 and the soft eyelet side is attached to the backside of sleeve 18. When the sleeves are crossed over in the front, the two pieces of the VELCRO ® fasteners will match up behind the infant's back and will attach the two sleeves together.

Garments constructed in accordance with this invention are advantageously made in at least two different sizes for premature babies and full term babies. By way of specific example, the garment sized for full term babies has a main body that approximates a rectangle of dimensions 21 inches long by 9 inches at its widest part. Each sleeve on the full term garment approximates a rectangle of 19 inches long by 4.5 inches at its widest part. The garment sized for premature babies, has a similarly shaped main body of 14 inches long by 6.5 inches wide with sleeves that are 12.5 inches long by 3.5 inches wide.

USE OF THE GARMENT

Figure 5:
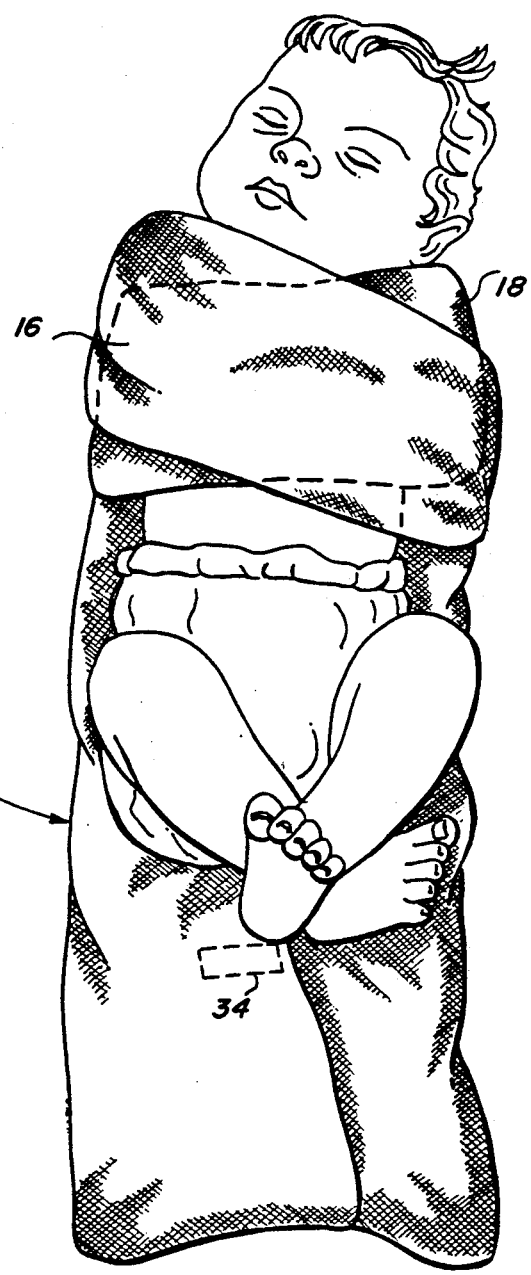
FIG. 5 is a front view of an infant in the garment with the legs removed from the main body of the garment while the infant's arms remain restrained within the sleeves of the garment.

As shown in FIG. 2, the two front panels 22, 26 are opened so the infant can be placed in the open pouch formed by the back panel 20 and two front panels joined along the sides and bottom. As shown in FIGS. 4, 5 the infants head extends through the neck opening 32, and the infant's arms are placed in the sleeves 16, 18. The frontal opening 14 is then secured in a closed position using the VELCRO® fasteners 34. With the infant's arms inside the sleeves 16, 18 the sleeves are used to position the infant's arms so they cross over each other with the elbows bent and gently rest in front of the infant's body thus assisting the infant in achieving the midline position as shown in FIG. 4. The extended sleeves 16, 18 are then wrapped around the infant and attached to each other in the back using the VELCRO® fastener 50, thus restraining the infant's arms in order to prevent any unnecessary motor releases.

A feature of the invention is that it provides ready access to the legs and body of the child as required for diaper changing or medical treatment. Thus, as shown in FIG. 5, the legs and body of the infant can be removed from the main body 12 of the garment 10 while the arms remain advantageously restrained in the sleeves 16, 18.

Another significant feature of this invention is that the electrical leads and tubes may be readily connected and unconnected to the infant. Thus, the monitoring electrical leads and tubes are lead through the spaces between the fasteners 34 so when the garment is closed the leads will pass through the frontal opening 14 without any problems. See FIG. 6 for an illustration of a child in the garment with tubes passing in between the fasteners 34 while the frontal opening 14 remains closed.

Figure 6:
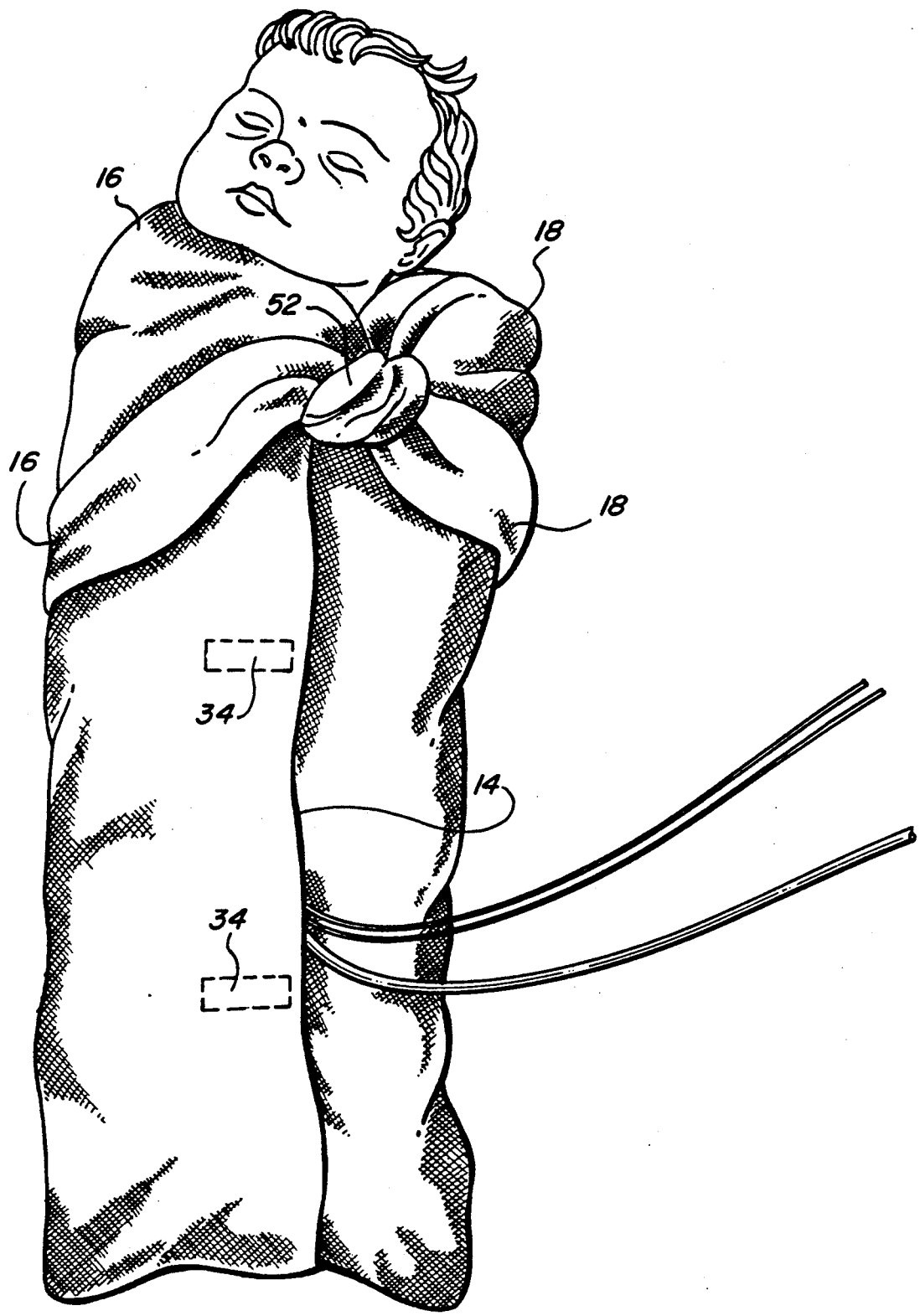
FIG. 6 is a frontal view of an infant placed in the garment illustrating the electrical monitoring leads and tubes extending from the frontal opening of the garment while the opening remains in a secured position. This figure also illustrates that the two sleeves may be tied in a knot and then secured behind the back of the infant to take up any additional slack in the sleeves.

As shown in FIG. 6, If the infant is so small that crossing the sleeves 16, 18 in back does not properly restrain the arms, then one sleeve may be crossed over the other in the front. The top sleeve should pass underneath the lower sleeve and then back out to form a knot 52. Both sleeves 16,18 wrap around the infant's body and fasten using the VELCRO® fasteners 50 in the back. The preferred embodiment is designed for a normal sized child, and can be adjusted to fit a variety of infants by fastening the VELCRO® fasteners in different locations along each of the fastening strips 34 and 50 or by tying the sleeves in a knot 52 to restrain the arms. If the child is extremely small or born prematurely, there is an additional embodiment that is sized especially for premature babies. Accordingly, the proportions of the garment can be adjusted to fit any infant.

USE OF THE INVENTION FOR CALMING DRUG ADDICTED INFANTS

The infant garment of the present invention provides for positioning and restraining the infant's arms in a crossed over bent elbow position, the midline position, and is demonstrated in FIG. 4. The sleeves 16, 18 have an extended length and are closed on the ends, so when the infants arms are placed in the sleeves they are restrained within the enclosed sleeve. The sleeves 16, 18 are sufficiently long so that, in use, they are crossed over, wrapped around the infant, and attached together behind the infant's back. The sleeves 16, 18 not only place the child in the midline position, but they are designed to hold the infant's arms in this position. The restraint of the infant's arms is especially important in the care of drug addicted infants that have a tendency to tremor and would not be able to maintain the midline position with out the help of this garment.

The main body 12 of the garment 10 is designed in a sac style in order to completely cover the infant's body while providing an open pouch for additional restraint of the infant's legs. The infant is free to curl up his legs to obtain a more comfortable midline position, but it is still restricted from too much movement. The VELCRO® fasteners 34 are designed to secure the frontal opening 14 of the garment 10 in a closed position. If the infant begins to shake or move around to much, he will not be able to uncover himself and thus will stay warm.

The opposing front panels 22, 26 when closed swaddle the infant between the front and back sides. By providing the infant with a warm comfortable garment that assists in the achievement and maintenance of the midline position, the infant rests more easily and saves its strength to aid in its development.

The present invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within their scope.

What is claimed:

1. The method for positioning an infant in the midline position to calm a drug addicted infant comprising the steps of:
   laying the infant into a garment having an open pouch, front panels which are closable, and sleeves which are longer than the arms of the infant;
   placing the infant's arms into said sleeves;
   closing said panels over the front of the infant to swaddle the entire body of the infant except the infant's head within said garment; and
   passing the end of each sleeve across the front of the infant and around the opposite side of the infant's body and attaching the remote ends of said sleeves together in the back of the infant so that the infant is positioned in the midline position with the infant's arms positioned in front of the infant in a crossed-over position with the elbows bent and with the infant free to curl up its body.

2. The method of calming an infant comprising the steps of:
   laying the infant into a garment having an open pouch and sleeves substantially longer than the arms of the infant;
   placing the infant's arms into said sleeves;
   passing the end of each sleeve across the front of the infant and around to the opposite side of the infant's body; and
   attaching said sleeves together in the back of the infant so that the infant is positioned in the midline position with the infant's arms positioned in front of the infant in a crossed-over position with the elbows bent and with the infant free to curl up its body.

3. The method for calming an infant comprising the steps of:
   swaddling the entire body of the infant except the infant's head between a back panel and a front panel of a garment;
   placing the infant's arms in sleeves substantially longer than the arms of the infant;
   passing the end of each sleeve across the front of the infant and around the opposite side of the infant's body; and attaching the remote ends of said sleeves together in the back of the infant.

4. The method for calming an infant comprising the steps of:
- swaddling the entire body of the infant except the infant's head between a back panel and a front panel of a garment;
- placing the infant's arms in sleeves substantially longer than the arms of the infant;
- crossing the arms of the infant over each other;
- tying the sleeves in a knot in the front of the garment;
- passing the end of each sleeve around to the opposite side of the infant's body; and
- attaching together the remote ends of said sleeves in the back of the infant.

5. The method for positioning an infant in the midline position to calm a drug addicted infant and provide easy and quick access to the infant for electrical heart leads, G.T. tubes and the like while restraining the infant from ripping out the leads and tubes by excessive arm and leg movement, comprising the steps of:
- laying the infant into a garment having an open pouch and sleeves substantially longer than the arms of the infant;
- placing the infant's arms into said sleeves;
- placing the infant's legs into said open pouch;
- passing the end of each sleeve across the front of the infant and around to the opposite side of the infant's body;
- attaching said sleeves together in the back of the infant; and
- attaching electrical leads, G.T. tubes and the like to the infant.

6. The method of claim 5 including the step of swaddling the infant by fastening front panels of said garment at locations spaced far enough apart to permit access for outside the garment to the inside of said garment for said electrical heart leads, G.T. tubes and the like.

7. The method of calming an infant comprising the steps of:
- laying the infant into a garment having sleeves substantially longer than the arms of the infant;
- placing the infant's arms into said sleeves;
- passing the end of each sleeve across the front of the infant and around to the opposite side of the infant's body; and
- attaching said sleeves together in the back of the infant so that the infant is positioned in the midline position with the infant's arms positioned in front of the infant in a crossed-over position with the elbows bent and with the infant free to curl up its body.

* * * * *